United States Patent [19]

Lancaster et al.

[11] 4,404,973

[45] Sep. 20, 1983

[54] HEART MUSCLE EVALUATION METHOD AND APPARATUS

[76] Inventors: Jack Lancaster, 1410 Park East, Garland, Tex. 75043; John Floyd, 9620 Greensprint, Dallas, Tex. 75238; William Harvey, 7016 Leameadow, Dallas, Tex. 75248

[21] Appl. No.: 255,895

[22] Filed: Apr. 20, 1981

[51] Int. Cl.³ .............................................. A61G 5/02
[52] U.S. Cl. ................................... 128/654; 128/659
[58] Field of Search .............. 128/654, 659, 713, 653; 364/417

[56] References Cited

U.S. PATENT DOCUMENTS

| | | | |
|---|---|---|---|
| 3,221,731 | 12/1965 | Annis et al. | 128/2.05 |
| 4,033,335 | 7/1977 | Nickles | 128/2.05 R |
| 4,181,939 | 1/1980 | Lyons | 364/200 |
| 4,245,646 | 1/1981 | Ionnou et al. | 128/653 |
| 4,294,259 | 10/1981 | Picunko et al. | 128/653 |

OTHER PUBLICATIONS

Nakomura, M. et al, "A Quanitative Approach for Correction of Background Counts: Determination of Left Ventricular Ejection Fraction by Radionuclide Angiocardiography," IEEE Transactions on Biomedical Engineering, vol. BME-29, No. 7, Jul. 1982, pp. 523-530.

Primary Examiner—Richard J. Apley
Assistant Examiner—George Yanulis
Attorney, Agent, or Firm—Hubbard, Thurman, Turner & Tucker

[57] ABSTRACT

A method and apparatus for evaluating the condition of the heart muscle utilizing a single roughly collimated radiation detector which is non-critically positioned over the heart muscle. A small amount of radioactive material is injected into the bloodstream and detected during the first transit through the heart. The background radiation level is empirically derived from, and may be utilized to correct, the aforementioned first transit data. Numerous parameters affecting the heart muscle may be determined by analysis of the resultant data.

16 Claims, 6 Drawing Figures

HEART MUSCLE EVALUATION METHOD AND APPARATUS

BACKGROUND OF THE INVENTION

This invention relates to a method and apparatus for evaluating the condition of the heart muscle in living beings, and more specifically to methods which utilize radioactive materials.

DESCRIPTION OF THE PRIOR ART

Attempts to evaluate the condition of the heart muscle, utilizing radioactive materials, are known in the prior art. One problem associated with such attempts involves the "background" radiation generated by radioactive material which is deposited into the body tissues and organs surrounding the heart during such testing. The inability to accurately categorize a portion of the radioactivity detected near the heart as attributable to this "background" level has long prevented accurate evaluation of the heart muscle utilizing these techniques. Several solutions to this problem have been attempted in the art. One example of an attempted solution may be seen in U.S. Pat. No. 3,221,731, issued to M. Annis et al. The Annis et al system utilizes two radiation detectors placed over the patient's body. One detector is utilized to detect radioactive activity in the heart, while the other detector is positioned away from the heart, to detect background radiation. The amount of background radiation is then subtracted from the radiation detected at the heart to achieve a more accurate reading.

A second example of a method utilized to distinguish background radiation may be seen in the "nuclear stethoscope" manufactured by BIOS, of Valhalla, New York. The "nuclear stethoscope" attempts to avoid background radiation problems as much as possible by utilizing a tightly focused or collimated radiation detector. While this tight focus does tend to decrease the background radiation, there are several problems inherent in this approach. The "nuclear stethoscope" requires a second reading in a location away from the heart to obtain a background level. Additionally, the sharply focused detector requires a critical positioning on the heart, a task made doubly difficult by individual variations in heart location and attitude. For a discussion of these problems see "Potential Pitfalls of the Nuclear Stethoscope," Michael J. Zema M.D. et al, J. B. Lippincott Company, 1980.

SUMMARY OF THE INVENTION

It is, therefore, one object of the invention to provide an apparatus for more accurate evaluation of the condition of the heart muscle.

It is another object of the invention to provide an apparatus for evaluation of the heart muscle which does not require critical positioning.

It is yet another object of the invention to provide an apparatus for evaluation of the heart muscle which requires a single detector positioned on the patient's body for a short period of time.

It is another object of this invention to provide an apparatus for evaluation of the heart muscle which requires injection of a small amount of radioactive material.

The foregoing objects are achieved as is now described. A roughly collimated radiation detector is noncritically positioned over the heart muscle. A small amount of radioactive material is injected into the bloodstream of the patient and the first transit of the material through the patient's heart is detected and analyzed. The background radiation level is empirically derived from the first transit data, and may be utilized to correct the data. The resultant data may then be analyzed to determine many parameters utilized to analyze heart functions.

BRIEF DESCRIPTION OF THE DRAWINGS

The novel features believed characteristic of the invention are set forth in the appended claims. The invention itself, however, as well as a preferred mode of use, further objects and advantages thereof, will best be understood by reference to the following detailed description of an illustrative embodiment when read in conjunction with the accompanying drawings, wherein:

DETAILED DESCRIPTION

Figure 1:
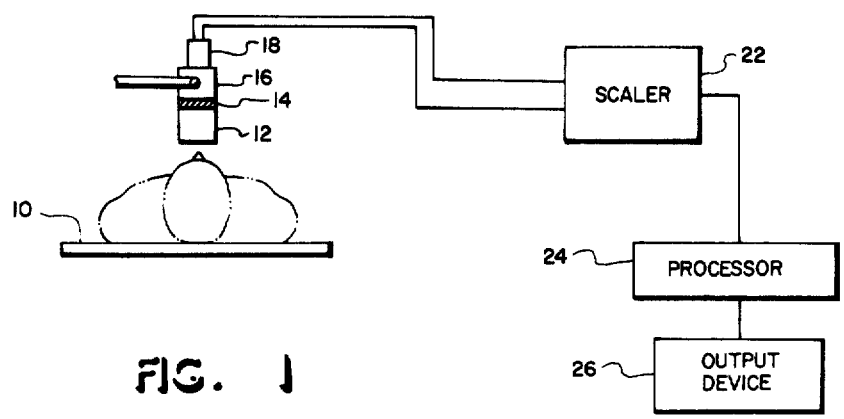
FIG. 1 is a partially diagrammatic and partially cross sectional view of the apparatus of the invention.

With reference now to FIG. 1, a patient's couch 10 is indicated, above which is located a single scanning detector. The scanning detector of a preferred embodiment utilizes a roughly focused lead collimator 12, capable of collimating incoming radiation from an area roughly the size of the human heart, at the average depth of the heart. By utilizing a roughly collimated scanning detector, the apparatus of this invention becomes relatively insensitive to variations in heart position and attitude. This non-critical positioning capability greatly enhances the utility of the apparatus of this invention by greatly diminishing the amount of training required to successfully operate the system. Above collimator 12 is a scintillation crystal 14, preferably of the sodium iodide, thallium activated type (NaI(Tl)), capable of converting the gamma radiation emitted by radioactive material into flashes of light. In the disclosed embodiment, an intravenous injection of approximately one mCi of Tc-99m is utilized to provide the radioactive agent. Associated with scintillation crystal 14, at the end of a light tight light pipe 16, is photomultiplier 18. Each light flash generated by scintillation crystal 14 is converted into an electron pulse and multiplied by photomultiplier 18. High gain rates possible in such photomultipliers yield a current pulse well above background.

These current pulses are applied to scaler 22 for scaling and amplification, and then coupled to processor 24. Processor 24 determines the background radiation level in a manner to be described herein in detail, and generates a desired parameter of heart muscle function. Desired parameters may be electronically visually displayed, recorded, or printed via output device 26.

Figure 2:
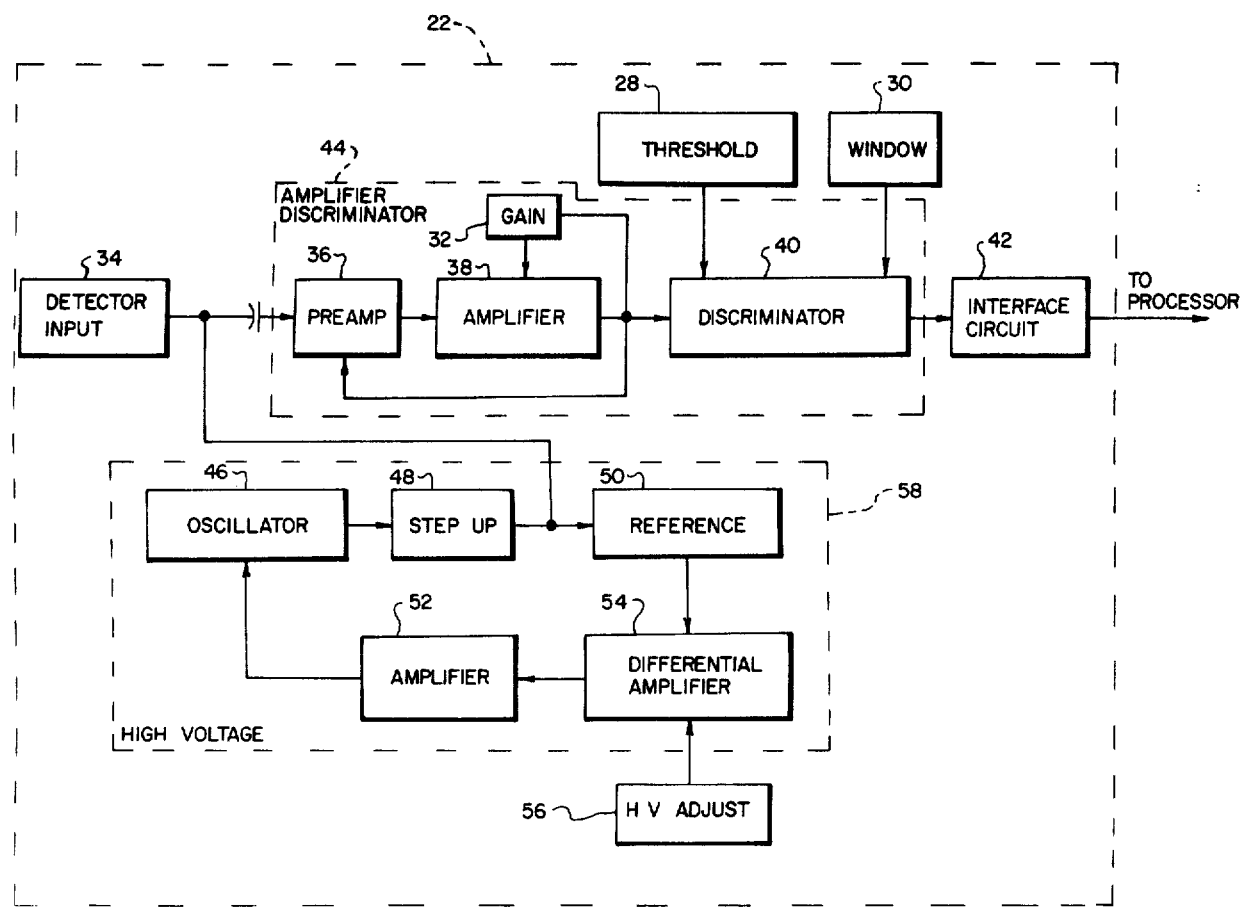
FIG. 2 is a block diagram of the major components of the scaler of FIG. 1.

Referring now to FIG. 2, there is depicted a block diagram of scaler 22. Scaler 22 includes two major sections; a high voltage supply 58 and an amplifier/discriminator 44. Amplifier/discriminator 44 includes a preamp 36 which integrates and differentiates the electron current generated by the scanning detector, generating a voltage pulse, the height of which is proportional to the energy of the gamma radiation interacting in scintillation crystal 14. This voltage pulse is further amplified by amplifier 38 and is applied to discriminator 40. Discriminator 40 acts as a pulse height analyzer and and accepts those pulses which vary a selected amount as valid inputs. In the embodiment disclosed, the median pulse height is representative of unscattered Tc-99m; however those skilled in the art will realize that this may vary for alternatively selected radioactive agents. The output of discriminator 40 is applied to an interface circuit 42 to create a TTL compatible pulse, in a manner well known in the art, for processor 24. In the embodiment disclosed, the minimum pulse width was constrained to 0.5 microseconds. The counting system utilized should be capable of attaining 200,000 counts per second without saturation. While various interface circuits may be utilized to compensate for alternative processor circuitry, the remaining elements of scaler 22 may be provided by commercially available systems. One example of such a system is the Model MS-2, Mini-Scaler, manufactured by the Eberline Instrument Corporation of Santa Fe, New Mexico.

Figure 3A:
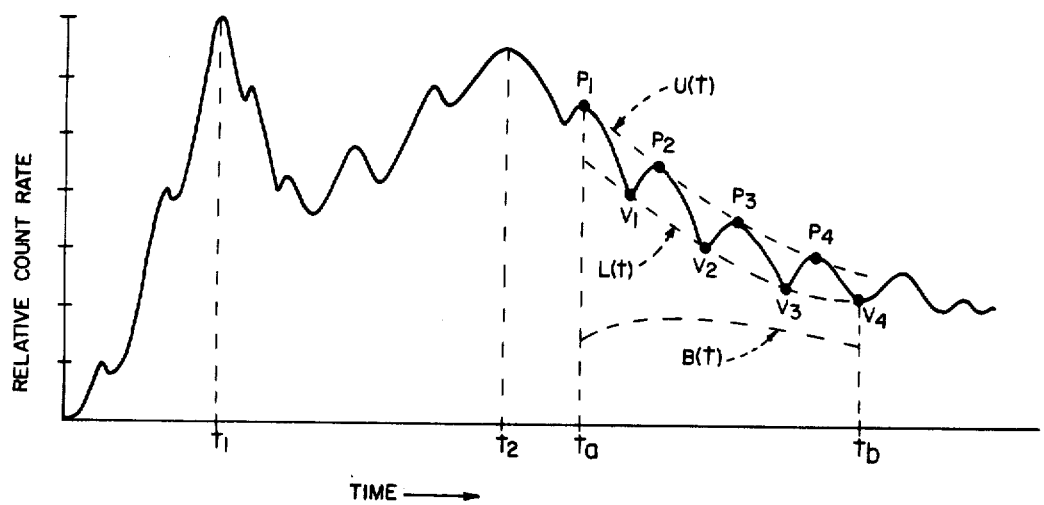
FIG. 3a is an average cardiac curve obtained by the apparatus of FIG. 1.

With reference now to FIG. 3a, there is depicted an average cardiac curve obtained utilizing the apparatus of this invention. The cardiac curve of FIG. 3a plots the relative count rate versus time. The first peak of radioactivity, occurring at time $t_1$ represents the bolus of radioactive material arriving at the right ventricle of the subject's heart. The radioactive level diminishes as the blood containing the injected material leaves the heart for the lungs, and then increases again as the material reenters the heart, into the left ventricle at time $t_2$. Those skilled in this art will appreciate that the difference between time $t_2$ and $t_1$ approximates the so-called "pulmonary transit" time. Individual variations present on the cardiac curve represent variations due to individual heartbeats. The method of determining the background radiation disclosed involves a calculation of the left ventricle ejection fraction (LVEF); however, in addition to the aforementioned pulmonary transit time, other cardiac functions may be determined utilizing the apparatus of this invention.

Figure 3B:
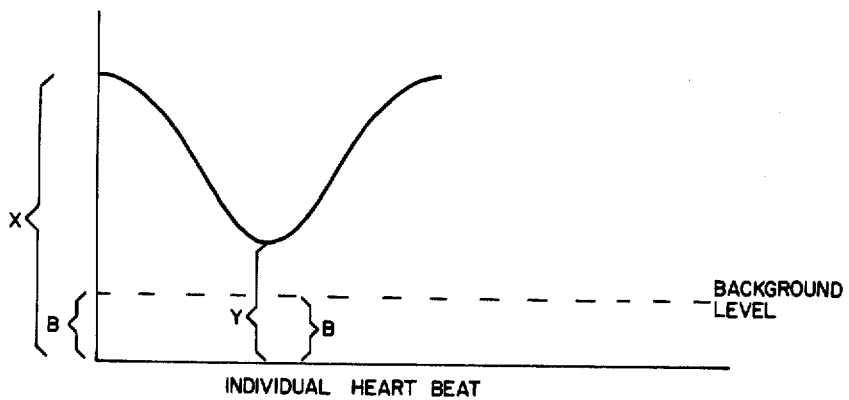
FIG. 3b is an average cardiac curve for a single heartbeat.

The left ventricle ejection fraction (LVEF) is a particularly useful parameter for determining the condition of the heart muscle. Referring now to FIG. 3b, we see a cardiac curve typical of a single heartbeat. The high points of the curve (when radiation is at the highest level) represent those periods when the heart is relaxed, and full of blood. This is referred to as the diastolic volume. The low point represents the contraction of the heart, and the radioactivity present in the heart at that point is proportional to the systolic volume, or the volume of blood present in the ventricle at the end of contraction. The LVEF is the ratio of the volume of blood pumped by the pumping chamber to the maximum volume of blood held by the pumping chamber. Thus, it should be clear that the LVEF will be a ratio, expressed as a decimal between zero and one. Referring again to FIG. 3b, we see that after correcting for background radiation due to the surrounding tissue and blood, (assumed to be a constant value B for this example) the LVEF may be expressed in terms of the labels of FIG. 3b as equation (1).

$$LVEF = \frac{X - Y}{X - B} \quad (1)$$

It should now be apparent that background correction is necessary for an accurate evaluation of the heart muscle.

Referring again to FIG. 3a, the method whereby the first transit data may be corrected to account for background radiation will be explained in detail. As explained earlier, at time $t_2$, the activity is seen to peak in the left ventricle. An assumption is made that at time $t_2$ the activity in the right ventricle is negligible. Therefore, at any point between time $t_a$ and time $t_b$, the detected radiation may be said to be attributable to the activity in the left ventricle of the heart at that point and the background radiation present in surrounding tissues and organs. Examining the cardiac curve of FIG. 3a, four representative relative peaks, $P_1$ through $P_4$, which occur during the time period $t_a - t_b$, are selected. These relative peaks represent those times when the heart is relaxed and full of blood. Similarly, four relative valleys, $V_1$ through $V_4$, are selected. Also seen in FIG. 3a is a curve B(t) which is assumed to approximate the values of background radiation during the selected time period. B(t) may be assumed to be expressible as a general second order function, as seen in Equation (2).

$$B(t) = B_2 t^2 + B_1 t + B_0 \quad (2)$$

Next, by any convenient method, the peak values, and valley values are each fitted to a similar second order function to create a single curve. These upper and lower curves are also assumed to be expressible as general second order functions as seen in Equations (3) and (4).

$$U(t) = U_2 t^2 + U_1 t + U_0 \quad (3)$$

$$L(t) = L_2 t^2 + L_1 t + L_0 \quad (4)$$

In the embodiment disclosed, processor 24 implements a simple least squares approximation of the desired functions, in the manner well known in the art. Having approximated the second order curves which best fit the peak values and the valley values, and having assumed a second order curve which fits the background function, the left ventricle ejection fraction may be expressed, as was discussed with respect to FIG. 3b, as seen in Equation (5).

$$LVEF = \frac{U(t) - L(t)}{U(t) - B(t)} \quad (5)$$

Further, the left ventricle ejection fraction may be assumed to be constant during the period in question, and therefore, the coefficients of the second order function B(t) may be expressed in terms of Equation (6), as simply derived from Equation (5).

$$B_n = U_n - \left(\frac{U_n - L_n}{LVEF}\right) \quad n = 0,1,2 \quad (6)$$

It will be appreciated by anyone skilled in the mathematics art that for every assumed value of LVEF in Equation (6), a corresponding value may be found for $B_n$. Therefore, a second relationship is necessary to correctly derive the background relationship. An advantageous relationship to consider at this point is a relationship of background activity to the activity taking place in the chamber of the heart. Recalling that background activity is generated as a result of radioactive material being deposited into the tissues and organs surrounding the heart, it should be apparent that the background activity at any given time period should be minimally correlated with, or independent of, the chamber activity during that time period. The instantaneous chamber activity may be easily expressed as the difference between the peak curve and the valley curve, of Equation (3) minus Equation (4). This relationship is expressed as the envelope function E(t), as seen in Equation (7).

$$E(t) = U(t) - L(t) \qquad (7)$$

Assuming that no correlation exists between the envelope function E(t) and the background function B(t), then the relationship seen in Equation (8) is true.

$$E\{B(t)\cdot E(t)\} = E\{B(t)\}\cdot E\{E(t)\} \qquad (8)$$

Where E {X} represents the expectation value of X over some unspecified range.

By forming a ratio R of the two sides of Equation (8) and integrating from time $t_a$ to time $t_b$, it can be seen that where B(t) and E(t) are minimally correlated, as assumed, the ratio R will approach unity. Utilizing these assumptions, it is a simple task for processor 24 to assume a value for LVEF and to calculate the corresponding values for B(t) and R, over the time period in question. A simple iterative approach will allow each possible value of LVEF and the corresponding value of B(t) to be derived. Having determined each possible corresponding set of LVEF values and B(t) values, ratio R is examined for each set to select the value of LVEF and B(t) for which ratio R most nearly approaches unity (indicating the minimal correlation relationship initially assumed).

Figure 4:
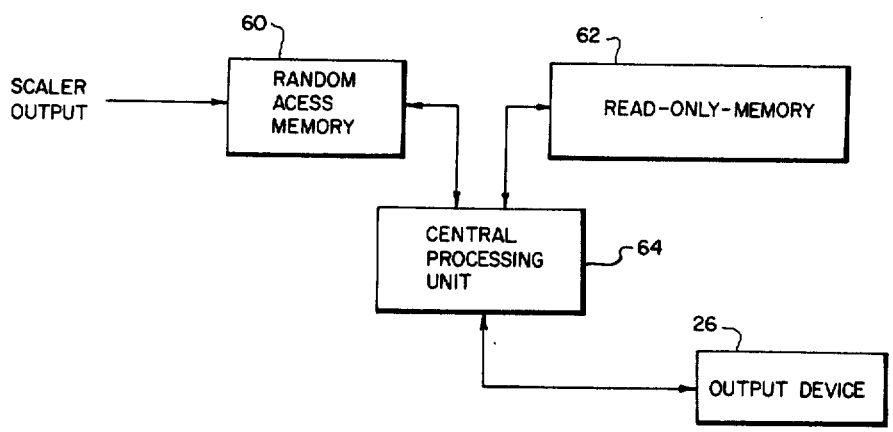
FIG. 4 is a block diagram of the major components of the processor of FIG. 1.

Referring now to FIG. 4, a block diagram of processor 24 is depicted. The count data generated by scaler 22 is stored in a Random-Access-Memory 60. A Central Processing Unit 64 operates upon the data in Random-Access-Memory 60 in a manner specified by an appropriate algorithm stored in Read-Only-Memory 62. Central Processing Unit 64 is preferably utilized to determine the second order functions necessary to describe the peak and valley curves, and to calculate and evaluate the equations required to determine the LVEF and background functions. A desired parameter may be electronically displayed, recorded or printed via output device 26. The prototype device, constructed for evaluation, utilized a standard micro or home-type computer to implement processor 24; however it is contemplated that a special purpose microprocessor programmed with a similar algorithm will possess those characteristics of processor 24 which are necessary for commercial implementation.

Figure 5:
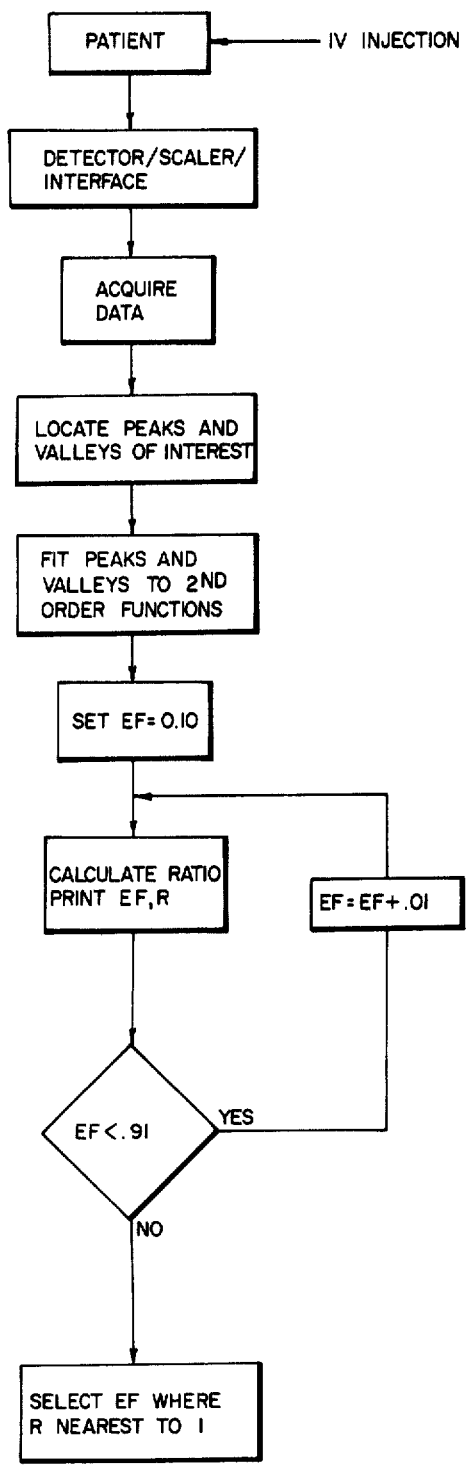
FIG. 5 is a flow chart diagram of the method and apparatus of the invention.

Referring now to FIG. 5, there is depicted a flow chart of the operation of the disclosed system. The flow chart begins with the intravenous injection of the radioactive agent into the patient. The detector/scaler is then utilized to detect and quantize the levels of radiation present in the patient's heart during the first transit of the radioactive material. The next two functions, acquiring data and locating the appropriate peaks and valleys, are controlled, in the embodiment disclosed, with the general purpose micro-computer. One example of a program for such data acquisition and plotting may be seen in Table I. The fitting of the peak and valley values to appropriate second order functions and the determination of which value for LVEF yields a minimal correlation between background activity and chamber activity may be accomplished by a program similar to that contained in Table II. It should be noted that in the embodiment disclosed, LVEF has been constrained to those values which fall between 0.10 and 0.90. It has been determined that the majority of patients will fall within these constraints; however, it would be a simple matter for those skilled in the art to narrow those constraints, or remove them entirely, with small adjustments to the program disclosed in Table II.

ALTERNATIVE EMBODIMENTS

Although the invention has been described with reference to a specific embodiment, this description is not meant to be construed in a limiting sense. Numerous technical advantages taught in the disclosed system will, upon reference to this description by persons skilled in the art, lend themselves to alternative embodiments of the invention. As an example, while the disclosed embodiment is described with reference to the calculation of the left ventricle ejection fraction, it should be apparent that the right ventricle ejection fraction may be similarly derived. Additionally, the pulmonary transit time parameter described herein may be derived utilizing the system disclosed, as well as a cardiac output index or other similar heart function parameters. It is therefore contemplated that the appended claims will cover any such modifications or embodiments that fall within the true scope of the invention.

TABLE I

```
5 PRINT""
10 PRINT"TIME/SAMPLE (2-65MILLISEC)";:INPUTT
20 PRINT"# OF 128-SAMPLE BLOCKS";:INPUTN
30 TL=1000*T:TU=INT(TL/256):TL=TL-256*TU:NBLK=31-N
40 POKE7938,TL:POKE7939,TU:POKE7940,NBLK:PRINT" "
50 PRINT"COLLECTION TIME = "; 128*T*N/1000
60 PRINT"TOTAL # SAMPLES = "; 128*N
70 PRINT"MEMORY REMAINING= "; 7167-256*N
80 PRINT" ":PRINT"ENTER 1 TO START";:INPUTA
90 IFA<>1THENPRINT"RE-ENTER ALL DATA!"
95 PRINT""
```

```
100 SYS7952
105 POKE245,14:PRINT" ":PRINT"BLOCK","COUNT"
110 POKE245,15
120 A=PEEK(2):IFA<NBLK THENPRINT"":GOTO200
125 PRINT"     ","     ";POKE245,15
130 PRINTA, 65535-256*PEEK(7943)-PEEK(7942):GOTO110
200 PRINT"":POKE245,10
201 POKE59467,0
203 SYS57825
204 STOP
205 PRINT"--PRINT ROUTINE":  PRINT"FROM $ TO $"
210 INPUTA,B
220 A=2*A:B=2*B
230 FORI=ATOBSTEP10
240 PRINTI/2;:FORJ=0TO8STEP2
245 B=7937-I-J
250 PRINTTAB(3*J);65535-256*PEEK(B)-PEEK(B-1);
260 NEXTJ:PRINT"":NEXTI
265 STOP
270 GOTO200
300 REM TAPE STORAGE
305 POKE243,122:POKE244,2
310 OPEN1,1,1,"HEART DATA"
320 FORI=1 TO 256*5
340 PRINT#1,PEEK(7936-I)
350 L=LEN(STR$(I))+1
360 GOSUB400
370 NEXTI
380 CLOSE1
390 GOTO500
400 REM    THIS IS A TAPE FIX SUBROUTINE
410 CH=CH+L
420 IFCH<192 THEN RETURN
430 TA=TI
440 POKE59411,53
450 IFTI-TA<10 THEN 450
460 POKE59411,61
470 CH=CH-191
480 RETURN
500 GOTO900
600 OPEN5,4
604 PRINT#5,CHR$(159)
605 PRINT"NUMBER OF SAMPLES";:INPUTN
610 FOR I=2 TO    2*N STEP32
615 PRINT#5,I/2,"     ",
620 FORJ=0 TO 30 STEP2
645 B=7937-I-J
650 Y=65535-256*PEEK(B)-PEEK(B-1)
660 PRINT#5,Y;:NEXTJ
670 PRINT#5,"   " :NEXTI
680 CLOSE5
690 GOTO900
700 OPEN5,4
710 ZR=0
715 DIMR(256)
720 G=158
725 T=159
728 PRINT#5,CHR$(G)
```

```
730 PRINT"NO. OF POINTS";:INPUT D
735 PRINT"DATA SCALE FACTOR";:INPUTF
740 FORI=2 TO 2*D STEP 14
745 FORZ=1TO256:R(Z)=ZR:NEXTZ
749 R(1)=64 :R(255)=127
750 FORJ=0 TO 12 STEP2
760 B=7937-I-J
765 Y=65535-256*PEEK(B)-PEEK(B-1)
767 Y=INT(Y/F)
769 IFY>255THENY=255
770 R(Y)=2^(6-J/2)
780 NEXTJ
795 FORZ=1TO256:PRINT#5,CHR$(R(Z));:NEXTZ
796 PRINT#5,CHR$(T),CHR$(G);
795 NEXTI
800 CLOSE5
900 PRINT"TAPE STORE=1,PRINT DATA=2,PLOTDATA=3"
910 PRINT"WHICH OPTION";:INPUTN
920 ON N GOTO 300,600,700
930 STOP
1000 END
```

TABLE II

```
70 DIMP(5);T(5),V(5),U(5)
100 PRINT"ENTER THREE PEAK AND VALLEY POINTS"
110 PRINT
120 FOR I=1 TO 3
130 PRINT"PEAK VALUE, TIME";
140 INPUT P(I),T(I)
150 PRINT
160 PRINT"VALLEY VALUE, TIME";
170 INPUT V(I),U(I)
180 PRINT
190 NEXTI
300 C1=C2=C3=C4=R0=R1=R2=0
320 FOR I=1 TO 3
330 C1=C1+T(I)
340 C2=C2+T(I)^2
350 C3=C3+T(I)^3
360 C4=C4+T(I)^4
370 R0=R0+P(I)
380 R1=R1+P(I)*T(I)
390 R2=R2+P(I)*(T(I)^2)
400 NEXTI
410 C0=3
420 E1=C1*C1-C0*C2
430 E2=C1*C2-C0*C3
440 F1=C2*C2-C1*C3
450 F2=C2*C3-C1*C4
460 S1=R0*C1-R1*C0
470 S2=R1*C2-R2*C1
480 A2=(S1*F1-S2*E1)/(F1*E2-F2*E1)
490 A1=(S1-E2*A2)/E1
500 A0=(R0-C2*A2-C1*A1)/C0
600 C6=C7=C8=C9=R5=R6=R7=0
610 FOR I=1 TO 3
```

```
820 C6=C6+U(I)
830 C7=C7+U(I)^2
840 C8=C8+U(I)^3
850 C9=C9+U(I)^4
860 R5=R5+U(I)
870 R6=R6+U(I)*U(I)
880 R7=R7+U(I)*(U(I)^2)
890 NEXTI
900 C5=7
910 E6=C9*C6-C5*C7
920 E7=C6*C7-C5*C8
930 F6=C7*C7-C6*C9
940 F7=C7*C8-C6*C9
950 S6=R5*C6-R6*C5
960 S7=R6*C7-R7*C6
970 B2=(S6*F6-S7*E6)/(F6*E7-F7*E6)
980 B1=(S6-E7*B2)/E6
990 B0=(R5-C7*B2-C6*B1)/C5
1000 PRINT"STARTING CORRELATION PHASE"
1005 OPEN5,4,1
1010 D2=A2-B2:D1=A1-B1:D0=A0-B0
1020 T5=T(3)^5-U(1)^5:T4=T(3)^4-U(1)^4
1030 T3=T(3)^3-U(1)^3:T2=T(3)^2-U(1)^2
1040 T1=T(3)-U(1)
1045 E=(D2*T3/3+D1*T2/2+D0*T1)
1050 FORJ=1 TO 80
1055 I=J/100
1060 C2=A2-D2/I:C1=A1-D1/I:C0=A0-D0/I
1070 N1=C2*D2*T5/5+(C2*D1+C1*D2)*T4/4
1080 N2=N1+(C2*D0+C1*D1+C0*D2)*T3/3
1090 N3=N2+(C1*D0+C0*D1)*T2/2
1092 N4=N3+C0*D0*T1
1095 N=N4/T1
1100 D=(C2*T3/3+C1*T2/2+C0*T1)*E/((T(3)-U(1))^2)
1110 R=N/D
1120 PRINT#5,"R=",R,"EF=",I
1130 NEXTJ
1500 STOP
2000 END
```

We claim:

1. An apparatus for evaluating the condition of the heart muscle for use in conjunction with means for injecting radioactive material into the bloodstream, said apparatus comprising:
   a single roughly collimated radiation detector adapted to be positioned near the heart muscle for simultaneously detecting radiation both within the heart muscle and in the vicinity of the heart muscle;
   means coupled to said detector for generating a plurality of signals indicative of the total amount of radiation detected; and
   processor means for processing said plurality of signals and for distinguishing in response to said processing radiation detected within the heart muscle from radiation detected in the vicinity of said heart muscle.

2. The apparatus according to claim 1, wherein said roughly collimated radiation detector is collimated to the approximate size of the human heart.

3. The apparatus according to claim 1 wherein said roughly collimated radiation detector comprises a sodium iodine, thallium activated radiation detector.

4. The apparatus according to claim 1, wherein said plurality of signals comprise a plurality of digital signals.

5. The apparatus according to claim 4, wherein said plurality of digital signals comprise a plurality of TTL compatible digital signals.

6. The apparatus according to claim 5, wherein said processor means comprises a digital computer.

7. The apparatus according to claim 1, wherein said processor means comprises a microprocessor.

8. An apparatus for evaluating a performance parameter of the heart muscle for use in conjunction with means for injecting radioactive material into the bloodstream, said apparatus comprising:
   a single roughly collimated radiation detector adapted to be positioned near the heart muscle for simultaneously detecting radiation both within the heart muscle and in the vicinity of the heart muscle;
   means coupled to said detector for generating a plurality of signals indicative of the total amount of radiation detected; and
   processor means for processing said plurality of signals, said processor means comprising:
   means for determining a level of radiation in the vicinity of the heart muscle which corresponds to each of a set of possible values of said performance parameter;
   means for selecting a level of radiation in the vicinity of the heart muscle which is least correlated with variations in said total amount of radiation detected; and
   means for determining a particular one of said set of possible values of said performance parameter which corresponds to said selected level of radiation in the vicinity of the heart muscle.

9. The apparatus according to claim 8, wherein said roughly collimated radiation detector is collimated to the approximate size of the human heart.

10. The apparatus according to claim 8, wherein said roughly collimated radiation detector comprises a sodium iodide, thallium activated radiation detector.

11. The apparatus according to claim 8, wherein said plurality of signals comprise a plurality of digital signals.

12. The apparatus according to claim 11, wherein said plurality of digital signals comprise a plurality of TTL compatible digital signals.

13. The apparatus according to claim 11, wherein said processor means comprises a digital computer.

14. The apparatus according to claim 8, wherein said processor means comprises a microprocessor.

15. A method for evaluating the condition of the heart muscle comprising the steps of:
   injecting a small amount of radioactive material into the bloodstream;
   positioning a roughly collimated radiation detector near the heart muscle;
   detecting and quantifying the level of radioactivity of the first transit of said radioactive material through the heart muscle;
   selecting a background level of radioactivity which is least correlated with the level of radioactivity within the heart muscle; and
   correcting said quantified level of radioactivity based upon said selected background level of radioactivity.

16. The method according to claim 15, further including the step of selecting a left ventricle ejection fraction which corresponds to said selected background level of radioactivity.

* * * * *